(12) United States Patent
Luhrs et al.

(10) Patent No.: US 8,455,548 B2
(45) Date of Patent: Jun. 4, 2013

(54) METHOD OF TREATING SENSORIMOTOR DISORDERS WITH ALPHA-2 ADRENERGIC RECEPTOR AGONISTS

(75) Inventors: Lauren M. B. Luhrs, Rancho Santa Margarita, CA (US); Daniel W. Gil, Corona Del Mar, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 62 days.

(21) Appl. No.: 12/680,640

(22) PCT Filed: Oct. 14, 2008

(86) PCT No.: PCT/US2008/079772
§ 371 (c)(1),
(2), (4) Date: Mar. 29, 2010

(87) PCT Pub. No.: WO2009/052073
PCT Pub. Date: Apr. 23, 2009

(65) Prior Publication Data
US 2010/0240699 A1    Sep. 23, 2010

Related U.S. Application Data

(60) Provisional application No. 60/981,029, filed on Oct. 18, 2007.

(51) Int. Cl.
*A01N 47/28* (2006.01)
*A61K 31/17* (2006.01)
*C07C 335/00* (2006.01)

(52) U.S. Cl.
USPC .......................................................... 514/580

(58) Field of Classification Search
USPC ..................... 514/580, 587; 564/17
See application file for complete search history.

(56) References Cited

U.S. PATENT DOCUMENTS

| | | | |
|---|---|---|---|
| 4,166,452 A | 9/1979 | Generales | |
| 4,256,108 A | 3/1981 | Theeuwes | |
| 4,265,874 A | 5/1981 | Bonsen et al. | |
| 6,329,369 B1 | 12/2001 | Chow et al. | |
| 6,534,542 B2 | 3/2003 | Chow et al. | |
| 6,545,182 B2 | 4/2003 | Chow et al. | |
| 6,787,517 B1 | 9/2004 | Gil et al. | |
| 6,841,684 B2 | 1/2005 | Chow et al. | |
| 7,091,232 B2 | 8/2006 | Chow et al. | |
| 7,141,597 B2 | 11/2006 | Chow et al. | |
| 7,276,522 B2 | 10/2007 | Heidelbaugh et al. | |
| 7,335,803 B2 | 2/2008 | Chow et al. | |
| 7,345,077 B2 | 3/2008 | Chow et al. | |
| 7,390,989 B2 | 6/2008 | Matiash et al. | |
| 7,399,868 B2 | 7/2008 | Heidelbaugh et al. | |
| 7,683,089 B1 | 3/2010 | Heidelbaugh et al. | |
| 2004/0132824 A1 | 7/2004 | Gil et al. | |
| 2004/0138312 A1 | 7/2004 | Wheeler et al. | |
| 2004/0266776 A1 | 12/2004 | Gil et al. | |
| 2005/0059664 A1 | 3/2005 | Gil et al. | |
| 2008/0103175 A1* | 5/2008 | Chow et al. .................. 514/314 |

FOREIGN PATENT DOCUMENTS

| WO | WO 01/78702 | 10/2001 |
|---|---|---|
| WO | WO 03/099795 | 10/2001 |

OTHER PUBLICATIONS

Jones et al. Biology 202, 2000 First Web Report, 2002, pp. 1-2.*
University of Maryland-Medical Reference. Patient Education, 2003, pp. 1-9.*
Messier et al., *Pharmacol. Toxicol.* 76:308-11 (1995).
Neve et al., *J. Biol. Chem.* 267:25748-25753 (1992).
Shimizu et al., *J. Neurochem.* 16:1609-1619 (1969).
Conklin et al., *Nature* 363:274-6 (1993).
*Remington's Pharmaceutical Sciences*, Mack Publishing Company, Easton, Pa., 16th Edition (1980).
Braff et al., *American Journal of Psychiatry*, 156:4: 596-602(1999).
Jankovic et al, Lancet Neurology, 5:10: 864-872 (2006).
U.S. Appl. No. 60/613,870, filed Sep. 28, 2004, Heidelbaugh et al.
U.S. Appl. No. 60/695,650, filed Jun. 29, 2005, Chow et al.
U.S. Appl. No. 60/747,444, filed May 17, 2006, Fang et al.
U.S. Appl. No. 60/884,718, filed Jan. 12, 2007, Heidelbaugh et al.
U.S. Appl. No. 60/917,828, filed May 14, 2007, Heidelbaugh et al.
U.S. Appl. No. 60/911,442, filed Apr. 12, 2007, Chow et al.
U.S. Appl. No. 60/911,478, filed Apr. 12, 2007, Chow et al.
U.S. Appl. No. 60/948,389, filed Jul. 6, 2007, Chow et al.

* cited by examiner

*Primary Examiner* — Samira Jean-Louis
(74) *Attorney, Agent, or Firm* — Krishna G. Banerjee

(57) ABSTRACT

Disclosed herein is a method of treating sensorimotor disorders comprising administering to a subject in need of such treatment an alpha-2 receptor agonist lacking significant alpha-2A receptor activity.

2 Claims, No Drawings

METHOD OF TREATING SENSORIMOTOR DISORDERS WITH ALPHA-2 ADRENERGIC RECEPTOR AGONISTS

CROSS-REFERENCE

This application claims the benefit of U.S. Application Ser. No. 60/981,029, filed Oct. 18, 2007, which is hereby incorporated by reference in its entirety.

Disclosed herein is a method of treating sensorimotor disorders by administering to a subject an alpha-2 adrenergic receptor agonist lacking significant alpha-2A receptor activity. Such agonists are effective in treating the disorders without sedating the patient to whom they are administered.

DETAILED DESCRIPTION OF THE INVENTION

Alpha-2 Receptor Agonists Lacking Significant Alpha-2A Activity

Alpha-2 receptor agonists are those compounds that activate alpha-2 adrenergic receptors. There are three subtypes of this receptor, designated A, B, and C. A compound is an "alpha-2B receptor agonist" if it has greater than 25% efficacy relative to brimonidine at the alpha-2B adrenergic receptor; a compound is an "alpha-2C receptor agonist" if it has greater than 25% efficacy relative to brimonidine at the alpha-2C adrenergic receptor; and a compound is an "alpha-2B/2C receptor agonist" if it has greater than 25% efficacy relative to brimonidine at both the alpha-2B and alpha-2C adrenergic receptors.

The methods of the present invention use alpha-2 agonists lacking significant activity at the alpha-2A receptor subtype. An agonist lacks significant alpha-2A receptor activity if the agonist has less than 40% of the efficacy of brimonidine at the alpha-2A receptor subtype. Compounds of the invention include, therefore, alpha-2B receptor agonists lacking significant alpha-2A activity; alpha 2B/2C receptor agonists lacking significant alpha-2A activity; and alpha-2C receptor agonists lacking significant alpha-2A activity. Any of the foregoing compounds may be used, even if they bind receptors other than alpha-2 receptors; for example, alpha-1 receptor agonists may be used, provided that the alpha-1 agonists also have greater than 25% efficacy relative to brimonidine at one or both of the alpha-2B and alpha-2C receptor subtypes, and lack significant alpha-2A receptor activity.

Efficacy, also known as intrinsic activity, is a measure of maximal receptor activation achieved by a compound and can be determined using any accepted assay of alpha-adrenergic receptor activation, such as a cAMP or Receptor Selection and Amplification Technology (RSAT). Efficacy is represented as a ratio or percentage of the maximal effect of the drug to the maximal effect of a standard agonist for each receptor subtype. Brimonidine, itself an alpha-2B receptor agonist (it is has 100% the efficacy of brimonidine at the alpha-2B adrenergic receptor), is used as the standard agonist for the alpha-2B adrenergic receptors.

Agonist activity can be characterized using any of a variety of routine assays, including, for example, Receptor Selection and Amplification Technology (RSAT) assays (Messier et al., *Pharmacol. Toxicol.* 76:308-11 (1995); cyclic AMP assays (Shimizu et al., *J. Neurochem.* 16:1609-1619 (1969)); and cytosensor microphysiometry assays (Neve et al., *J. Biol. Chem.* 267:25748-25753 (1992)). Such assays generally are performed using cells that naturally express only a single alpha-adrenergic receptor subtype, or using transfected cells expressing a single recombinant alpha-adrenergic receptor subtype. The adrenergic receptor can be a human receptor or homolog of a human receptor having a similar pharmacology.

The RSAT assay measures receptor-mediated loss of contact inhibition resulting in selective proliferation of receptor-containing cells in a mixed population of confluent cells. The increase in cell number is assessed with an appropriate detectable marker gene such as beta-galactosidase, if desired, in a high throughput or ultra high throughput assay format. Receptors that activate the G protein, Gq, elicit the proliferative response. Alpha-adrenergic receptors, which normally couple to Gi, activate the RSAT response when coexpressed with a hybrid Gq protein containing a Gi receptor recognition domain, designated Gq/i5. Conklin et al., *Nature* 363:274-6 (1993)).

As an example, an RSAT assay can be performed essentially as follows. NIH-3T3 cells are plated at a density of $2\times10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 µg), receptor (1-2 µg) and G protein (1-2 µg). Carrier DNA, for example 40 µg salmon sperm DNA, also can be included to increase transfection efficiency. Fresh media is added on the following day; one to two days later, cells are harvested and frozen in 50 assay aliquots. Transfected cells are thawed, and 100 µl of cells added to 100 µl aliquots of compound to be tested, with various concentrations assayed in triplicate, for example, in 96-well plates. Incubation continues for 72 to 96 hours at 37° C. After washing with phosphate-buffered saline, β-galactosidase activity is determined by adding 200 µl of chromogenic substrate (3.5 mM O-nitrophenyl-β-D-galactopyranoside/0.5% NP-40 in phosphate buffered saline), incubating overnight at 30° C., and measuring optical density at 420 nm. The absorbancy is a measure of enzyme activity, which depends on cell number and reflects receptor-mediated cell proliferation. The $EC_{50}$ and maximal effect (i.e., efficacy) of each drug at each receptor is determined.

Alpha-2B and -2C receptor agonists lacking significant alpha-2A receptor activity are known in the art. Detailed information regarding alpha-2 agonists, including their structure, synthesis, and activity, may be found in U.S. Pat. Nos. 6,329,369, 6,534,542, 6,545,182, 6,787,517, 6,841,684, and 7,091,232; in U.S. Patent Application Publication No. 2003/0092766, No. 2004/0132824, No. 2004/0220402, No. 2005/0075366, and No. 2005/0267186; and in U.S. patent application Ser. No. 11/172,229, Ser. No. 11/232,323, Ser. No. 11/232,341, No. 60/613,870, No. 60/695,650, No. 60/747,444, No. 60/884,718, No. 60/917,828, No. 60/911,422, No. 60/911,478, and No. 60/948,389, the disclosures of all which are incorporated herein by reference.

One can use in the methods of the invention any pharmaceutically acceptable salt, prodrug, isomer, or racemate of any alpha-2 receptor agonist lacking significant alpha-2A receptor activity.

Pharmaceutically Acceptable Salts

Alpha-2 receptor agonists may be used as their pharmaceutically acceptable salts.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Prodrugs

One can use in the compositions and methods of the invention a prodrug of any alpha-2 receptor agonist.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e., the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

The alpha-2 receptor agonists of the invention may be either synthetically produced, or may be produced within the body after administration of a prodrug. Hence, the term "alpha-2 receptor agonist" encompasses both compounds produced by a manufacturing process and those compounds formed in vivo only when another drug administered.

Isomers and Racemates

One can use in the compositions and methods of the invention an enantiomer, stereoisomer, or other isomer of an alpha-2 receptor agonist. One can also use in the compositions and methods of the invention a racemic mixture or one or both racemates, in any proportion.

Dose

The precise dose and frequency of administration depends on the severity and nature of the patient's condition, on the manner of administration, on the potency and pharmacodynamics of the particular compound employed, and on the judgment of the prescribing physician. Determining dose is a routine matter that is well within the capability of someone of ordinary skill in the art. In general, alpha-2 receptor agonists are administered in therapeutically effective doses, that is, at a dose that is sufficient to produce the desired therapeutic effect.

Excipients and Dosage Forms

Those skilled in the art will readily understand that alpha-2 receptor agonists can be admixed with pharmaceutically acceptable excipients which are well known in the art.

A pharmaceutical composition to be administered systemically may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. No. 4,256,108, No. 4,166,452, and No. 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

Sensorimotor Disorders

Compounds of the invention are useful in treating sensorimotor disorders. To "treat," as used here, means to deal with medically. It includes administering an alpha-2B receptor agonist to prevent the onset of a condition, to diminish its severity, and to prevent its reoccurrence. The inventors have discovered that compounds of the invention may be used to treat sensorimotor disorders without causing the sedation that ordinarily accompanies the administration of alpha-2 agonists.

A "sensorimotor disorder" is any condition characterized by abnormal motor output in response to sensory input information. Such disorders are caused by a deficit in sensorimotor gating, the ability of the central nervous system to process sensory input information. Sensorimotor disorders are therefore distinguished from other movement disorders by their cause: a deficit in processing sensory input information creates an urge to perform a motion, whereas in other disorders, movement arises independently of any urges to perform them or other consequences of sensorimotor gating. In this sense, the movements of sensorimotor disorders may not be strictly involuntary, but, rather, merely difficult to suppress. For the purposes of this invention such movements need only interfere with a patient's normal functioning or otherwise be undesirable.

Sensorimotor disorders include or are associated with the following, for example: Tourette's syndrome, transient tic disorder, trichotillomania, attention deficit/hyperactivity disorder (combined type, predominantly hyperactive-compulsive type, predominantly inattentive type, and not otherwise specified ("NOS")), amphetamine-induced disorders (anxiety, mood and NOS), cocaine-induced disorders (anxiety, mood and NOS), PCP-induced disorders (anxiety, mood and NOS), other (or unknown) substance-induced disorders (anxiety, mood and NOS), post-traumatic stress disorder, autism, and psychoses, such as schizophrenia and other conditions characterized by hallucinations and delusions.

In one embodiment of the invention, a sensorimotor disorder is further characterized by changes (for example, an increase or a decrease) in the availability or utilization of dopamine in the nervous system; hence, compounds of the invention may be used to treat sensorimotor disorders in which hyper- or hypo-dopamine conditions play a role in the etiology of the disorder.

In another embodiment of the invention, a sensorimotor disorder is further characterized by defects in prepulse inhibition. In normal subjects, a startle reflex induced by a particular stimulus (pulse) is reduced when the stimulus is preceded by a milder stimulus (prepulse). In a subject with a sensorimotor disorder, the prepulse does not have this effect or its effects are diminished. Prepulse inhibition is a highly validated task that is commonly found to be deficient in various neuropsychiatric disorders such as Tourette's syndrome, schizophrenia, autism, and attention deficit-hyperactivity disorder. A subject experiencing undesired movements who has deficiencies in prepulse inhibition may be presumed to have a sensorimotor disorder.

Methods of assessing prepulse inhibition in human patients is well known in the art. One method, for example, is described in detail in D. L. Braff et al., *American Journal of Psychiatry*, 156:4 (1999). According to this method, blinking, a component of the startle response, is measured by electromyogram activity transmitted via electrodes positioned over the orbicularis oculi muscle. Subjects are acclimated for five minutes against a continuing background of 70 dB[A] continuous SPL broadband noise. and then proceed to two blocks of trials, with each trial being performed six times, as shown in Table 1.

TABLE 1 experimental protocol for assessing prepulse inhibition. The startle pulse is 40 msec of 118-dB[A] SPL bursts of noise, and the prepulse is given as dB[A] above the 70 dB[A] background. Each trial is separated by 15 seconds.

| BLOCK | TRIAL | MEASURE |
|---|---|---|
| 1 | 1-6 | Startle pulse alone |
|   | 7-12 | 2-dB[A] prepulse followed by startle pulse |
|   | 13-18 | 4-dB[A] prepulse followed by startle pulse |
|   | 19-24 | 8-dB[A] prepulse followed by startle pulse |
|   | 25-30 | 16-dB[A] prepulse followed by startle pulse |
|   |   | No stimulus |
| 2 | 1-6 | Startle pulse alone |
|   | 7-12 | 2-dB[A] prepulse followed by startle pulse |
|   | 13-18 | 4-dB[A] prepulse followed by startle pulse |
|   | 19-24 | 8-dB[A] prepulse followed by startle pulse |
|   | 25-30 | 16-dB[A] prepulse followed by startle pulse |

The compounds of the invention may be used to treat any individual, presenting with undesired movements, who shows deficiencies in prepulse inhibition compared to normal subjects tested pursuant to the above protocol.

EXAMPLES

The invention is illustrated by the following examples. This is provided for illustration only; many more embodiments are possible.

Amphetamine-Induced Stereotypy and Pre-Pulse Inhibition of the Startle Response

Activity in these sensorimotor tasks was exemplified with two different alpha-2B receptor agonist pharmacophores: Compound A, a thiourea, and Compound B, an imidazole thione, both of which lack significant alpha-2A receptor activity.

General Findings

Amphetamine-induced stereotypy is a model of increased dopamine-mediated perseverative behaviors. In this model, Compounds A and B were able to effectively inhibit stereotypy associated with high-dose psychostimulant administration. Compound A was also evaluated in the pre-pulse inhibition of the startle response task. Compound A significantly inhibited the disruption of PPI induced by the psychostimulants amphetamine, apomorphine, and phencyclidine.

Importantly, these compounds are orally active, and therefore could be administered in solution, tablet or capsule.

Table 2, below, shows the structures of Compounds A and B.

| COMPOUND | COMPOUND STRUCTURE |
|---|---|
| A | HO—CH₂CH₂—NH—C(=S)—NH—CH₂—(2-F,3-Cl-phenyl) |
| B | 2-tetralone substituted with CH₂-(2-thioxo-imidazol-4-yl) |

Alpha-2B Receptor Agonists Selectively Inhibit Amphetamine-Induced Stereotypy

C57B/6 male mice were placed in an open field apparatus and allowed to habituate for 15-30 minutes. Compounds A or B were administered PO at 0, +15, or +30 minutes relative to amphetamine (8 mg/kg) administration (Compound B was also administered 15 minutes pre-amphetamine), and locomotor behavior was scored for an additional 60 minutes post-amphetamine. Amphetamine was administered IP. Locomotion was separated into "fine movements" (indicative of stereotypy) and "ambulations" (indicative of hyperactivity).

The alpha-2B receptor agonists selectively decreased amphetamine-induced stereotypy, as shown in the following table.

TABLE 3

| GROUP | TIME POST-AMPHETAMINE (MIN) | FINE MOVEMENTS | AMBULATIONS |
|---|---|---|---|
| Vehicle + Vehicle | | 740.3 ± 59.5 | 3633.2 ± 946.6 |
| Amphetamine + Vehicle | | 3375.2 ± 323.4 | 7428.2 ± 577.4* |
| Compound A + Amphetamine | 0 | 810.1 ± 112.5◊ | 6338.0 ± 714.1* |
| | 15 | 1312.9 ± 205.2◊ | 14056.6 ± 708.7* |
| | 30 | 2581.3 ± 359.1 | 7494.6 ± 612.3* |
| Compound B + Amphetamine | −15 | 937.3 ± 47.3◊ | 7258.8 ± 672.4* |
| | 0 | 736.7 ± 103.4◊ | 9954.8 ± 1042.9* |
| | 15 | 1096.3 ± 79.2◊ | 7226.2 ± 457.3* |
| | 30 | 1284.8 ± 48.8◊ | 8453.8 ± 461.7* |

◊ indicates significant difference relative to the respective vehicle + amphetamine group.
*indicates significant difference relative to the vehicle + vehicle group.

Alpha-2B Receptor Agonists Restore PPI Disrupted by Psychostimulants

Male Sprague-Dawley rats were treated with Drug 1 (IP) followed 20 minutes later by Drug 2 (IP or SC as indicated in the methods). Ten minutes following administration of Drug 2 (except in the case of apomorphine where animals were immediately tested post-apomorphine), rats were placed in the startle chamber and allowed 5 minutes to acclimate with 65-dB background white noise. The acclimation period was followed by a ~15 minute test session during which time rats were presented with 40 ms 120 dB startle pulses alone or preceded 100 ms by a pre-pulse 3, 6, or 12 dB above background. These four types of active stimuli were presented in pseudorandom order along with no-stimulation trials to assess baseline activity throughout testing. An average of 20 s separated each trial type. The maximum startle magnitude was measured for every trial type. PPI for each animal was calculated as the percentage startle magnitude to the pre-pulse+pulse or no-stimulation trials relative to the pulse-alone startle magnitude. * and ** indicate differences relative to vehicle+vehicle-treated animals ($P<0.05$ and $P<0.01$, respectively).

TABLE 4

Compounds A and B restore PPI

| DRUG 1 | DRUG 2 | % PPI | | |
|---|---|---|---|---|
| | | PP3 | PP6 | PP12 |
| Vehicle | Vehicle | 40.1 ± 6.3% | 45.3 ± 4.6% | 64.4 ± 3.3% |
| Vehicle | Amph (2 mg/kg) | 24.7 ± 7.4% | 28.6 ± 4.9%* | 43.2 ± 7.3%* |
| Clonidine (0.03 mg/kg) | | 21.8 ± 9.1% | 35.5 ± 8.6% | 51.3 ± 10.5% |
| Compound A (100 ug/kg) | | 38.6 ± 7.1% | 50.2 ± 4.7% | 68.5 ± 3.3% |
| Compound B (10 ug/kg) | | 28.2 ± 7.4% | 30.9 ± 6.2%* | 46.9 ± 7.6%* |
| Compound B (30 ug/kg) | | 25.3 ± 9.2% | 48.6 ± 5.3% | 60.0 ± 3.4% |
| Compound B (100 ug/kg) | | 34.5 ± 5.7% | 45.3 ± 7.4% | 67.0 ± 6.4% |
| Vehicle | Apo (0.5 mg/kg) | 23.6 ± 8.9% | 38.6 ± 3.9% | 43.2 ± 5.3%* |
| Clonidine (30 ug/kg) | | 20.0 ± 10.6% | 31.5 ± 11.0% | 24.5 ± 16.1%** |
| Compound A (30 ug/kg) | | 38.5 ± 7.7% | 53.8 ± 6.2% | 58.9 ± 3.8% |
| Vehicle | PCP (2 mg/kg) | 27.3 ± 8.1% | 28.9 ± 10.2% | 40.6 ± 9.5%* |
| Clonidine (30 ug/kg) | | 31.7 ± 13.5% | 30.1 ± 13.1% | 53.7 ± 8.8% |
| Compound A (30 ug/kg) | | 40.2 ± 7.5% | 50.6 ± 5.5% | 62.9 ± 4.2% |

Methods

Amphetamine induced stereotypy. C57B/6 male mice were placed in an open field apparatus and allowed to habituate for 15-30 minutes. Compounds A or B were administered at 0, +15, or +30 minutes relative to amphetamine (8 mg/kg) administration (Compound B was also administered 15 minutes pre-amphetamine), and locomotor behavior was scored for an additional 60 minutes post-amphetamine. Locomotion was separated into "fine movements" (indicative of stereotypy) and "ambulations" (indicative of hyperactivity).

Prepulse inhibition of the startle response. Sprague Dawley male rats (~250 g-300 g) are used (n=8/group). Rats are administered drug 1 (vehicle, Compound A, Compound B, or clonidine) followed 20 minutes later by amphetamine (2 mg/kg, s.c.), apomorphine (0.5 mg/kg s.c), PCP (2 mg/kg i.p.) or vehicle (0.9% NaCl, s.c.). Either immediately (apomorphine) or 10 minutes (amphetamine, PCP, or vehicle) following injection of drug 2, animals are placed in the SR-Lab startle chamber (San Diego Instruments, San Diego Calif.). Each rat is acclimated to the chamber for 5 minutes with 65 dB background noise. This acclimation period is followed by a ~15 minute PPI test session where rats are presented with 120 dB startle pulses without a pre-pulse or pulses preceded by a pre-pulse of 3, 6, or 12 dB above background noise. These active stimuli are presented in pseudorandom order along with no-sound trials, with an average of 20 sec separating each trial (range 5-27 seconds). A sensor in the chamber records the startle magnitude following all stimuli presented. % PPI represents the percentage startle magnitude to the pre-pulse+pulse or no-stim trials relative to the pulse-alone startle magnitude.

The alpha 2B compounds were administered i.p. or p.o., PCP was administered i.p., and apomorphine and amphetamine were administered s.c.

What is claimed is:

1. A method of treating a sensorimotor disorder, wherein said sensorimotor disorder is selected from or is associated with a disorder selected from the group consisting of autism, and amphetamine-induced anxiety and mood disorders, comprising administering to a subject in need of such treatment a compound of the formula:

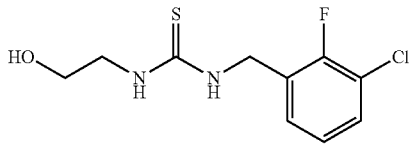 [SMILES: OCCNC(=S)NCc1cccc(Cl)c1F]

or a pharmaceutically acceptable salt thereof; wherein said "treating" refers to diminishing the severity of said disorder and to preventing its reoccurrence.

2. The method of claim 1, wherein said treatment takes place without causing sedation.

* * * * *